United States Patent
Kim et al.

(10) Patent No.: US 11,925,920 B2
(45) Date of Patent: Mar. 12, 2024

(54) CATALYST FOR HYDROGENATION OF AROMATIC COMPOUND AND PREPARATION METHOD THEREFOR

(71) Applicant: HANWHA CHEMICAL CORPORATION, Seoul (KR)

(72) Inventors: Eung Gyu Kim, Daejeon (KR); Won Yong Kim, Seoul (KR); Jeong Hwan Chun, Yongin-si (KR); Young Jin Cho, Yongin-si (KR); Joung Woo Han, Yangju-si (KR); Hyo Suk Kim, Daejeon (KR); Wan Jae Myeong, Daejeon (KR); Ki Taeg Jung, Daejeon (KR)

(73) Assignee: HANWHA CHEMICAL CORPORATION, Seoul (KR)

( * ) Notice: Subject to any disclaimer, the term of this patent is extended or adjusted under 35 U.S.C. 154(b) by 0 days.

(21) Appl. No.: 16/761,898

(22) PCT Filed: Oct. 16, 2018

(86) PCT No.: PCT/KR2018/012203
§ 371 (c)(1),
(2) Date: May 6, 2020

(87) PCT Pub. No.: WO2019/088513
PCT Pub. Date: May 9, 2019

(65) Prior Publication Data
US 2020/0316564 A1    Oct. 8, 2020

(30) Foreign Application Priority Data
Nov. 6, 2017  (KR) .................. 10-2017-0146916

(51) Int. Cl.
*B01J 21/10* (2006.01)
*B01J 23/00* (2006.01)
(Continued)

(52) U.S. Cl.
CPC .............. *B01J 21/10* (2013.01); *B01J 23/005* (2013.01); *B01J 23/462* (2013.01); *B01J 35/008* (2013.01);
(Continued)

(58) Field of Classification Search
CPC ...... B01J 23/005; B01J 23/462; B01J 35/008; B01J 35/026; B01J 35/1014; B01J 35/1019; B01J 35/1042; B01J 35/1047
See application file for complete search history.

(56) References Cited

U.S. PATENT DOCUMENTS 3,751,508 A * 8/1973 Jiang et al. ............ B01J 23/755
                                                       585/262
7,208,545 B1   4/2007 Brunner et al.
(Continued)

FOREIGN PATENT DOCUMENTS

CN    104923270 A  *  9/2015 .............. B01J 21/12
CN    105327701 A     2/2016
(Continued)

OTHER PUBLICATIONS

Human translation of Zhou et al. (Liquid-Phase Partial Hydrogenation of Benzene over Ru/MgAl2O4 Catalyst: Effect of Calcination Temperature of MgAl2O4, Chinese Journal of Catalysis, vol. 32 No. 9 (2011) 1537-1544), published 2011.*
(Continued)

*Primary Examiner* — Jun Li
(74) *Attorney, Agent, or Firm* — Sughrue Mion, PLLC

(57) ABSTRACT

The present invention relates to a catalyst for hydrogenation of an aromatic compound, which is capable of greatly reducing the inactivation of a catalyst by using a support including a magnesium-based spinel structure, and a preparation method therefor.

5 Claims, 1 Drawing Sheet

(51) Int. Cl.
    *B01J 23/46*      (2006.01)
    *B01J 35/00*      (2006.01)
    *B01J 35/02*      (2006.01)
    *B01J 35/10*      (2006.01)
    *C07C 67/283*      (2006.01)
    *C07C 69/75*      (2006.01)

(52) U.S. Cl.
CPC ......... *B01J 35/026* (2013.01); *B01J 35/1014* (2013.01); *B01J 35/1019* (2013.01); *B01J 35/1042* (2013.01); *B01J 35/1047* (2013.01); *C07C 67/283* (2013.01); *C07C 69/75* (2013.01)

(56) References Cited

U.S. PATENT DOCUMENTS

| | | | |
|---|---|---|---|
| 2004/0034252 A1* | 2/2004 | Stochniol | C07C 209/72 564/450 |
| 2004/0232049 A1* | 11/2004 | Dath | C10G 45/46 208/143 |
| 2016/0280629 A1 | 9/2016 | Jung et al. | |

FOREIGN PATENT DOCUMENTS

| | | | | |
|---|---|---|---|---|
| CN | 104549236 B | * | 3/2017 | |
| CN | 107159314 A | * | 9/2017 | ............. B01J 21/04 |
| EP | 0 167 996 A1 | | 1/1986 | |
| JP | 47-6858 A | | 4/1972 | |
| JP | 10-128117 A | | 5/1998 | |
| JP | 2004-168777 A | | 6/2004 | |
| JP | 2012130895 A | * | 7/2012 | |
| JP | 2016-539106 A | | 12/2016 | |
| KR | 10-2004-0089207 A | | 10/2004 | |
| KR | 10-0464581 B1 | | 12/2004 | |
| KR | 10-2005-0083906 A | | 8/2005 | |
| KR | 10-0688403 B1 | | 2/2007 | |
| KR | 10-0893794 B1 | | 4/2009 | |

OTHER PUBLICATIONS

Machine translation of Jiang et al.(CN107159314A), publication date Sep. 15, 2017.*

Zhou Gongbing et al., "Liquid-Phase Partial Hydrogenation of Benzene over Ru/MgAl2O4 Catalyst : Effect of Calcination Temperature of MgAl2O4", Chinese Journal of Catalysis, 2011, pp. 1537-1544, vol. 32.

Yan Feng et al., "Effect of the Degree of Dispersion of Pt over MgAl2O4 on the Catalytic Hydrogenation of Benzaldehyde", Chinese Journal of Catalysis, Sep. 2017, pp. 1613-1620, vol. 38.

International Search Report for PCT/KR2018/012203 dated Apr. 12, 2019 [PCT/ISA/210].

Written Opinion of the International Search Authority dated Apr. 12, 2019 [PCT/ISA/237].

Manori J. Silva et al., "Identification of potential biomarkers of exposure to di(isononyl)cyclohexane-1,2-dicarboxylate (DINCH), an alternative for phthalate plasticizers", Journal of Exposure Science and Environmental Epidemiology, 2012, vol. 22, No. 2, pp. 204-211 (8 pages).

Basagiannis A C et al., "Influence of the carrier on steam reforming of acetic acid over Ru-based catalysts", Applied Catalysis B. Environmental, Elsevier, Amsterdam, NL, vol. 82, 2008, pp. 77-88 (12 pages).

Szmigiel D et al., "Ammonia decomposition over the ruthenium catalysts deposited on magnesium-aluminum spinel", Applied Catalysis A: General, Elsevier, Amsterdam, NL, vol. 264, 2004, pp. 59-63 (5 pages).

* cited by examiner

CATALYST FOR HYDROGENATION OF AROMATIC COMPOUND AND PREPARATION METHOD THEREFOR

CROSS REFERENCE TO RELATED APPLICATIONS

This application is a National Stage of International Application No. PCT/KR2018/012203 filed Oct. 16, 2018, claiming priority based on Korean Patent Application No. 10-2017-0146916 filed Nov. 6, 2017.

TECHNICAL FIELD

The present invention relates to a catalyst for hydrogenation of an aromatic compound and a preparation method therefor, and more particularly, to a catalyst for hydrogenation of an aromatic compound, which is capable of greatly reducing inactivation of a catalyst by using a support including a magnesium-based spinel structure, and a preparation method therefor.

BACKGROUND ART

Phthalate-based compounds are a material widely used as a plasticizer for plastics, especially polyvinyl chloride (PVC). For example, phthalate-based compounds are used for various purposes, for example, electrical and electronic products, medicines, paint pigments, lubricants, binders, surfactants, adhesives, tiles, food containers, packaging materials, and the like.

However, some phthalate-based compounds are known as a material that causes environmental pollution and endocrine disrupter in humans. Thus, efforts to reduce the use of phthalate-based compounds have been made to strengthen regulations on use, especially in developed countries such as Europe and the United States. In particular, some products such as di(2-ethylhexyl)phthalate (DEHP), butyl benzyl phthalate (BBP), di-n-butylphthalate (DBP), and diisononyl phthalate (DINP) among phthalate-based plasticizers are suspected of environmental hormones as endocrine disrupters that socially interfere with or disrupt the human hormone action, and thus, there is a movement to regulate their use.

Accordingly, efforts have been made to develop eco-friendly plasticizers free from the environmental hormone debate while showing the same performance as conventional plasticizers. One of them is a method of using a compound obtained by hydrogenating a benzene ring contained in a phthalate-based compound.

For a hydrogenation reaction of an aromatic compound such as a benzene ring, a method of using a catalyst in which an active component, that is, a transition metal such as ruthenium is supported on a support is known.

In this regard, Korean Patent Registration No. 10-0464581 discloses the use of an alumina support in which 30% to 40% of a pore volume of a support is made of macropores having a pore diameter in a range of 50 nm to 10,000 nm and 60% to 70% of the pore volume of the support is made of mesopores having a pore diameter in a range of 2 nm to 50 nm.

In addition, Korean Patent Registration No. 10-0688403 discloses a patent for use as a plasticizer in a catalyst prepared by applying an active metal containing ruthenium on a support containing macropores, a novel hydrogenation product obtained by hydrogenating a benzene polycarboxylic acid (derivative), and plastics.

Furthermore, Korean Patent Registration No. 10-0893794 discloses a catalyst in which ruthenium is supported on a silica support, thereby showing improved activity and high product selectivity in hydrogenation of monosaccharide and oligosaccharide.

However, in the conventional catalyst of the transition metal described above, the activity is rapidly reduced as the reaction progresses, resulting in a reduction in yield. Therefore, the maintenance of the catalytic activity is a very important issue in industrial terms. The reduction in catalytic activity is the result of various physical and chemical effects on the catalyst, for example, thermal, mechanical, or chemical treatment and is caused by blocking or loss of catalytically active sites. For example, catalyst inactivation or aging is generally caused by sintering of the catalytically active site or loss of metal as the result of deposits, or poisoning of the active site, and a variety of mechanisms exist. The catalyst replacement and regeneration process due to the reduced activity of the catalyst leads to an increase in the production cost of the product.

Therefore, in order to produce a material capable of being usable as an eco-friendly plasticizer on a commercial scale, there is a need for a method for improving the performance of a catalyst used in a hydrogenation reaction and maintaining excellent activity to increase the life time of the catalyst.

DESCRIPTION OF EMBODIMENTS

Technical Problem

The present invention aims to solve the above-described problems of the related art and the technical problems requested from the past.

An object of the present invention is to provide a catalyst for hydrogenation of an aromatic compound, which includes a magnesium-based spinel structure, thereby greatly reducing the inactivation of a catalyst by hydrogenating aromatics in an organic compound, and a preparation method therefor.

Solution to Problem

To achieve such an object, the present invention provides a catalyst for hydrogenation of an aromatic compound,
  wherein the catalyst includes a catalytically active component and a support, and
  the support includes a compound of Formula 1 having a magnesium-based spinel structure:

$$Mg_xAl_2O_{3+x} \qquad \text{[Formula 1]}$$

wherein x is an integer from 0.1 to 1.0.

In one preferred embodiment of the present invention, the support may include at least one active metal selected from the group consisting of ruthenium, palladium, rhodium, platinum, nickel, and any mixture thereof.

In one preferred embodiment of the present invention, an amount of the active metal may be in a range of 0.1 wt % to 10 wt %.

In one preferred embodiment of the present invention, ruthenium (Ru) or ruthenium oxide ($RuO_2$) may be supported on the support having the spinel structure.

In one preferred embodiment of the present invention, the support may include 0 wt % to 5 wt % of magnesium oxide (MgO).

In one preferred embodiment of the present invention, the catalyst may be in at least one form selected from powder, particle, granular, and molded supports.

In one preferred embodiment of the present invention, the catalytically active component may be supported on the support in a form of a metal salt solution to prepare a precursor.

In one preferred embodiment of the present invention, the catalyst may be an egg-shell type catalyst.

In one preferred embodiment of the present invention, the egg-shell type catalyst may have a pore volume of 0.1 ml/g to 1.5 ml/g and a BET surface area of 10 m²/g to 300 m²/g.

In one preferred embodiment of the present invention, a Mg/Al molar ratio may be 0.0625 to 0.5.

Meanwhile, the present invention provides a hydrogenation method of an aromatic compound used for hydrogenation of an organic compound containing an aromatic ring by using a catalyst and a cyclohexane polycarboxylic acid or cyclohexane polycarboxylic acid derivative prepared using the same.

The present invention provides cyclohexane-1,2-dicarboxylic acid di(isopentyl) ester obtained by hydrogenating n-pentyl-isopentyl-phthalate, cyclohexane-1,2-dicarboxylic acid di(isoheptyl) ester obtained by hydrogenating diisoheptylphthalate, cyclohexane-1,2-dicarboxylic acid di(isononyl) ester obtained by hydrogenating diisononylphthalate, cyclohexane 1,2-dicarboxylic acid (2-ethylhexyl) ester obtained by hydrogenating bis(2-ethylhexyl) phthalate, and di(2-ethylhexyl) cyclohexane-1,4-dicarboxylate (DEHCH) obtained by hydrogenating dioctyl terephthalate ((bis(2-ethylhexyl) benzene-1,4-dicarboxylate).

Advantageous Effects of Disclosure

As described above, the hydrogenation catalyst according to the present invention includes the support including the magnesium-based spinel structure, thereby greatly reducing the inactivation of the catalyst by hydrogenating aromatics in the organic compound.

BEST MODE

Figure 1:
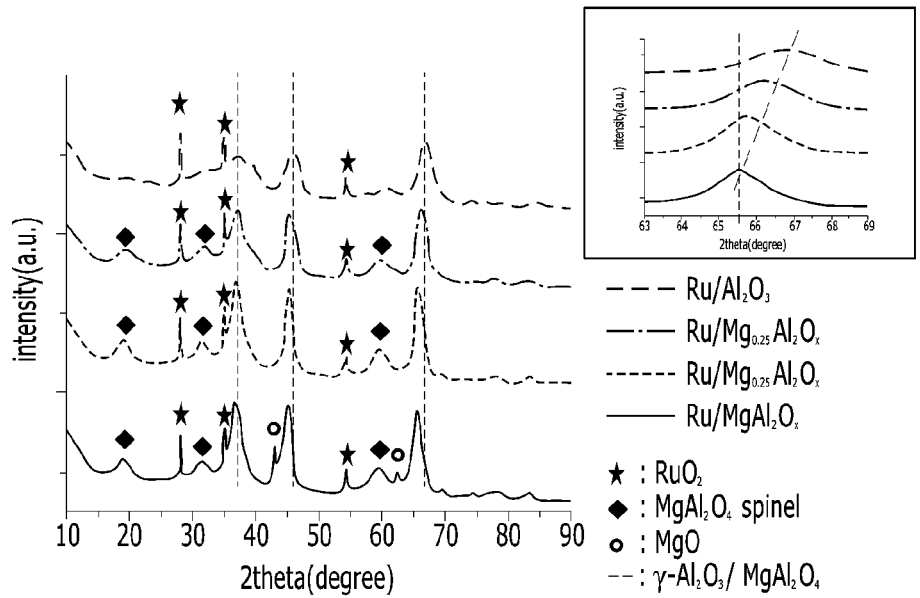
FIG. 1 is a graph showing a result of XRD analysis of a Mg-introduced spinel support according to the present invention.

The present invention will be described with reference to specific embodiments and the accompanying drawings. The embodiments will be described in detail in such a manner that the present invention may be carried out by those of ordinary skill in the art. It should be understood that various embodiments of the present invention are different, but need not be mutually exclusive. For example, certain shapes, structures, and features described herein may be implemented in other embodiments without departing from the spirit and scope of the present invention in connection with one embodiment.

Therefore, the following detailed description is not to be taken in a limiting sense, and the scope of the present invention is to be limited only by the appended claims and the entire scope of equivalents thereof, if properly explained.

Hereinafter, embodiments of the present invention will be described with reference to the accompanying drawings, so that those of ordinary skill in the art can easily carry out the present invention.

As described above, when the conventional egg-shell type catalyst used in the hydrogenation process is inactivated during the hydrogenation reaction according to the type of the catalyst, causing the cost of catalyst replacement, the reduction in operating time, and the like.

In the present invention, the solution to the above-described problems has been sought by including a support including a magnesium-based spinel structure to significantly reduce inactivation of a catalyst by hydrogenating aromatics in an organic compound.

The present invention provides a catalyst for hydrogenation of an aromatic compound, wherein the catalyst includes a catalytically active component and a support, and the support includes a compound of Formula 1 having a magnesium-based spinel structure.

$$Mg_xAl_2O_{3+x}$$ [Formula 1]

wherein x is an integer from 0.1 to 1.

According to the present invention, the catalytically active component may be supported on the support in the form of a metal salt solution to prepare a precursor.

Specifically, the support includes at least one active metal selected from the group consisting of ruthenium, palladium, rhodium, platinum, nickel, and any mixture thereof. An amount of the active metal may be in a range of preferably 0.1 wt % to 10 w %, and more preferably 0.3 wt % to 5 wt %.

According to the present invention, the support may be supported on the support having the spinel structure, for example, ruthenium (Ru) or ruthenium oxide (RuO$_2$). The support may include 0 wt % to 5 wt % of magnesium oxide (MgO).

At this time, when the magnesium oxide (MgO) is included in excess of 5 wt %, the activity of the catalyst may be reduced, or a side reaction may occur. Therefore, the above range is particularly preferable.

On the other hand, the catalyst according to the present invention may be in the powder, particle, granular, or molded form. Preferably, the catalyst according to the present invention is in the molded form.

Hereinafter, the structure and operation of the present invention will be described in more detail with reference to preferred examples of the present invention. However, these example are shown by way of illustration and should not be construed as limiting the present invention in any way.

Since contents not described herein can be sufficiently technically inferred by those of ordinary skill in the art, descriptions thereof will be omitted.

EXAMPLES

<Example 1> Preparation of Mg$_x$Al$_2$O$_{3+x}$ Support Having Spinel Structure In order to adjust a Mg/Al molar ratio to a desired ratio in an alumina pellet support for structural transformation (1:2 for MgAl$_2$O$_4$ spinel), a necessary magnesium precursor and an aqueous solution in which the magnesium precursor was dissolved in excess distilled water were added and dried in a forced convection hot air oven at 120° C. Then, the dried support was calcined at a constant temperature in an electric furnace under air flow and slowly cooled to room temperature to finally obtain a Mg$_x$Al$_2$O$_{3+x}$ support having a spinel structure. An XRD analysis was performed on the structure of the support manufactured in this manner and results thereof are shown in FIG. 1. The results of nitrogen adsorption/desorption of the support and the pore volume calculation results obtained through water absorption are shown in Table 1 below.

TABLE 1

| Support | Specific surface area (m²/g) | Pore volume (cm³/g) |
|---|---|---|
| γ-Al$_2$O$_3$ | 237.1 | 1.01 |
| Mg$_{0.25}$Al$_2$O$_x$ | 203.7 | 0.95 |
| Mg$_{0.5}$Al$_2$O$_x$ | 160.2 | 0.84 |
| MgAl$_2$O$_x$ | 100.5 | 0.68 |

As shown in FIG. 1, in the case of γ-alumina, peaks exist at about 32.6°, 37°, 39.2°, 45° to 46°, and 67°, and in the case of the structurally transformed support, peaks exist at about 19°, 31.5°, 45°, 59.5°, and 66°. Thus, it can be confirmed that as the amount of Mg introduced increased, the structure was transformed into the spinel structure.

<Example 2> Preparation of Catalyst in which Ruthenium Nanoparticles were Supported on Support A ruthenium precursor was measured so that a weight of ruthenium in a supported catalyst became 1 wt %. A volume of an aqueous solution was adjusted so as to be 97% of a pore volume of a support (alumina or structurally transformed Mg$_x$Al$_2$O$_{3+x}$ support). Then, a precious metal was supported on the support through an incipient wetness impregnation method. The supported catalyst was dried in a forced convection hot air oven at 120° C. The dried catalyst was calcined at 400° C. in an electric furnace under air flow and slowly cooled to room temperature to finally obtain a catalyst in which ruthenium was supported on the support.

Figure 2:
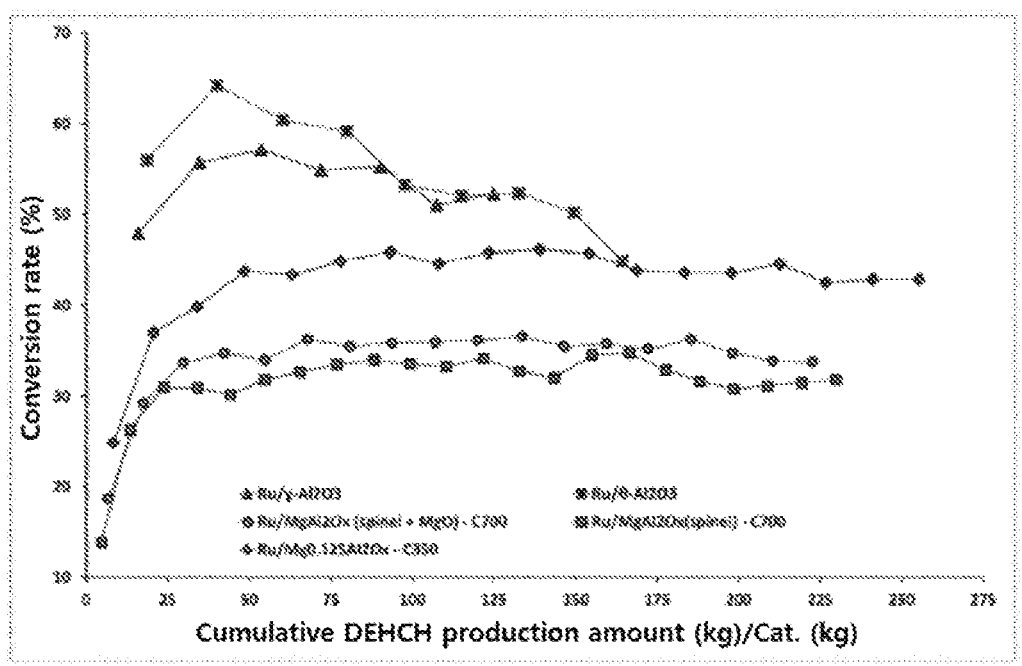
FIG. 2 is a graph showing a result of a reaction experiment for each support during the preparation of a catalyst according to the present invention.

<Example 3> DOTP (Dioctyl Terephthalate) Hydrogenation Reaction in Batch Reactor Using Catalyst Prepared Through the Above Method 6 cc of the catalyst prepared in Example 2 was filled in a catalyst basket mounted on a magnedrive. In a 300-mL batch reactor (autoclave), a reaction was performed with a 250-mL dioctyl terephthalate solution at 150 bar H$_2$ at a temperature of 180° C. for 1 hour and 30 minutes. After the reaction, the hydrogen pressure was released and the product was removed from the reactor. The same amount of DOTP was put again and a reaction was performed again several times. By using this, a conversion rate of the catalyst in a continuous batch reactor was measured and results thereof are shown in FIG. 2.

Comparative Example

<Comparative Example 1> Preparation of Catalyst in which Ruthenium Nanoparticles were Supported on γ-Alumina Support A ruthenium precursor was measured so that a weight of ruthenium in a γ-alumina support became 1 wt %. A volume of an aqueous solution was adjusted so as to be 97% of a pore volume of the support. Then, a precious metal was supported on the support through an incipient wetness impregnation method. Then, the supported catalyst was dried in a forced convection hot air oven at 120° C. The dried catalyst was calcined at 400° C. in an electric furnace under air flow and slowly cooled to room temperature to finally obtain a catalyst in which ruthenium was supported on the support.

Experimental Example

A Mg(NO$_3$)$_2$ aqueous solution was added to an Al$_2$O$_3$ alumina support and dried and calcined to prepare a catalyst support having a Mg$_x$Al$_2$O$_{3+x}$ type spinel structure. The support was supported with a RuNO(NO$_3$)$_3$ aqueous solution and drying calcination was performed thereon to prepare a RuO$_2$/Mg$_x$Al$_2$O$_{3+x}$ catalyst. The prepared catalyst was used to perform a hydrogenation reaction on DOTP (dioctyl terephthalate) in an autoclave and a trickle bed reactor to prepare DEHCH (di(2-ethylhexyl)-1,4-cyclohexane dicarboxylate).

As shown in Table 2 below, as a result of observing catalyst inactivation according to the number of times of reactions in an autoclave reaction, it was confirmed that the inactivation of the catalyst supported using γ- and θ-alumina as a support appeared rapidly, but in the present invention, the inactivation expressed as a decrease in the average conversion rate of the catalyst prepared using Mg$_x$Al$_2$O$_{3+x}$ or MgOMg$_x$Al$_2$O$_{3+x}$ as a support was significantly reduced.

TABLE 2

| Catalyst | Ini conv. | Max conv. | Max Number of times | Min conv. | Min Number of times | Reduction in average conversion rate (Inactivation degree) (%)/number of times |
|---|---|---|---|---|---|---|
| Ru/γ-Al$_2$O$_3$ | 48 | 57 | 3 | 51 | 6 | 2.0 |
| Ru/θ-Al$_2$O$_3$ | 56 | 64 | 2 | 44 | 9 | 2.8 |
| Ru/MgAl$_2$O$_x$(MgO)-C700 | 18.5 | 36.3 | 6 | 33.8 | 18 | 0.2 |
| Ru/MgAl$_2$O$_x$(S.S)-C700 | 13.9 | 34 | 9 | 31.8 | 22 | 0.2 |
| Ru/Mg$_{0.125}$Al$_2$O$_x$-C350 | 24.9 | 45.9 | 7 | 42.9 | 18 | 0.3 |

While the present invention has been described by particular matters such as specific components and limited embodiments and drawings, this is provided only for helping the comprehensive understanding of the present invention. The present invention is not limited to the above-described embodiments, and it will be understood by those of ordinary skill in the art that various modifications and variations can be made thereto without departing from the scope of the present invention.

Therefore, it will be understood that the spirit of the present invention should not be limited to the above-described embodiments and the claims and all equivalent modifications fall within the scope of the present invention.

The invention claimed is:

1. A catalyst for hydrogenation of an aromatic compound, the catalyst comprising an active metal and a support,
   wherein the support includes a compound of Formula 1 having a magnesium-based spinel structure:

$$Mg_xAl_2O_{3+x} \qquad \text{[Formula 1]}$$

wherein x is from 0.125 to 0.25,
   a Mg/Al molar ratio is 0.0625 to 0.125,
   the active metal is comprised in an amount of 0.3 wt % to 5 wt % in the catalyst, the active metal is ruthenium (Ru), and
ruthenium (Ru) or ruthenium oxide ($RuO_2$) is supported on the support having the spinel structure, and
wherein the catalyst is an egg-shell type catalyst, and the egg-shell type catalyst has a pore volume of 0.95 ml/g to 1.5 ml/g and a BET surface area of 203.7 $m^2$/g to 300 $m^2$/g.

2. The catalyst of claim 1, wherein the support comprises 0 wt % to 5 wt % of magnesium oxide (MgO).

3. The catalyst of claim 1, wherein the catalyst is in at least one form selected from powder, particle, granular, and molded supports.

4. The catalyst of claim 1, wherein the active metal is supported on the support in a form of a metal salt solution to prepare a precursor.

5. A hydrogenation method comprising conducting hydrogenation of dioctyl terephthalate (DOTP) in the presence of the catalyst of claim 1, under 150 bar $H_2$ and 180° C. to produce Di(2-ethylhexyl)cyclohexane-1,4-dicarboxylate (DEHCH).

* * * * *